(12) United States Patent
Ritter et al.

(10) Patent No.: US 6,776,568 B2
(45) Date of Patent: Aug. 17, 2004

(54) TREATMENT OF WASTE MATERIALS

(75) Inventors: Russell Anthony Ritter, Scone (AU); Anthony Martin Niederberger, Waverton (AU); Barry James Smith, Eastwood (AU); Mike Lotzof, Balmain (AU); Kelvin Bannister, Woodberry (AU)

(73) Assignee: Vermitech Pty Limited, New South Wales (AU)

( * ) Notice: Subject to any disclaimer, the term of this patent is extended or adjusted under 35 U.S.C. 154(b) by 0 days.

(21) Appl. No.: 10/410,010

(22) Filed: Apr. 8, 2003

(65) Prior Publication Data

US 2003/0207443 A1 Nov. 6, 2003

Related U.S. Application Data

(62) Division of application No. 09/623,695, filed as application No. PCT/AU99/00238 on Mar. 31, 1999, now Pat. No. 6,548,294.

(30) Foreign Application Priority Data

Apr. 6, 1998 (AU) ................................................ PP2828

(51) Int. Cl.[7] .................................................. C05F 9/02
(52) U.S. Cl. ........................ 414/287; 414/306; 414/308; 414/324
(58) Field of Search ................................ 414/324, 327, 414/287, 304, 306, 308

(56) References Cited

U.S. PATENT DOCUMENTS

| | | | | |
|---|---|---|---|---|
| 2,695,107 A | * | 11/1954 | Baker | 414/306 |
| 4,198,186 A | * | 4/1980 | Holdren et al. | 414/308 |
| 5,527,373 A | * | 6/1996 | Chareyre | 71/9 |
| 6,648,254 B2 | * | 11/2003 | Hruska | 241/101.763 |

FOREIGN PATENT DOCUMENTS

| | | | |
|---|---|---|---|
| AU | 199894187 A1 | * | 6/1999 |
| CA | 2170294 | * | 8/1977 |
| EP | 0 887 328 A2 | * | 12/1998 |

* cited by examiner

Primary Examiner—Thomas J. Brahan
(74) Attorney, Agent, or Firm—Cesari and McKenna, LLP (57) ABSTRACT

Apparatus suitable for use in the treatment of waste and/or organic materials which includes a main body having a treatment chamber therein having a base which when the apparatus is in a harvesting mode is arranged with a space there below. The base includes a plurality of generally parallel spaced apart support elements, the support elements being spaced apart at a distance sufficient to support the material within the chamber during the treatment process and enable extraction of the treated material through the spaces between the support elements during a harvesting process. There is also disclosed a harvesting device comprising a plurality of extraction elements which are adapted to project through the spaces between the support elements to dislodge and extract the treated material through the base. The apparatus and harvesting device is particularly useful for removing worm casting in vermiculture.

15 Claims, 14 Drawing Sheets

TREATMENT OF WASTE MATERIALS

CROSS-REFERENCE TO RELATED APPLICATIONS

This application is a division of Ser. No. 09/623,695, filed Sep. 1, 2000, now U.S. Pat. No. 6,548,294 which is a 371 of PCT/AU99/00238 filed Mar. 31, 1999.

BACKGROUND OF THE INVENTION

This invention relates generally to the treatment of waste materials and more particularly, though not exclusively, to the treatment of organic waste material such as for example, sewage sludge.

One particular application of the present invention relates to the treatment of organic waste materials by the use of worm species. This process is referred to hereinafter as vermiculture. Vermiculture is a process by which organic material is fed to a variety of worm species with the purpose of converting the organic material into increased worm biomass and vermicast. Vermicast is the excreter from worms and has use as a plant growth medium and soil conditioner. The worm biomass can be used for bait, animal feed and domestic and small composting systems. Worms have the ability to convert a wide range of organic material including sewage sludge provided the material is presented in an acceptable form. Vermiculture has been used in the past for the stabilization of sewage sludge and other organic waste however, previous systems have been on a small scale and not be considered economically viable.

It is an object according to one aspect of the invention to provide apparatus suitable for use in vermiculture processing which enables large scale treatment of waste materials.

According to one aspect of the present invention there is provided apparatus suitable for use in the treatment chamber of waste and/or organic materials, the apparatus including a main body having a treatment chamber therein which includes a base which when the apparatus is in a harvesting mode is arranged with a space therebelow, the base including a plurality of generally parallel spaced apart support elements, the support elements being spaced apart at a distance sufficient to support the material within the chamber during the treatment process and enable extraction of the treated material through the spaces between the support elements during a harvesting process.

Preferably, the treatment chamber is at least partially bounded by a side wall and the support elements extend across the chamber between opposed sections of the side wall thereby defining the spaces between adjacent support elements.

Preferably, the base includes openings at the opposed sections of the side wall, each opening being associated with and generally aligned with a respective one of the spaces between adjacent support elements, the openings extending from the support elements in the direction of the side wall. It will be appreciated that the support elements may extend longitudinally of the main body.

Preferably, the space between the elements, center to center, is about from 50 mm to 100 mm, more preferably, from 70 or 80 mm to 90 mm and even more preferably from 85 mm to 90 mm.

The support elements may be in the form of elongated bars or rods which may be about 12 mm in cross-sectional dimension. The support elements are preferably of formed metal and more preferably steel, such as for example, 500 mpa yield strength steel.

In one preferred form of the invention, the support elements are in the form of substantially U-shaped rods or bars, the spaces between the uprightly directed arms of each U-shaped element defining the openings referred to earlier.

The main body may be in the form of a generally box like structure which is preferably of a general rectangularly or square shape when viewed in plan and has an open top. The apparatus may include a plurality of such structures in the form of modular units which can be arranged side by side. The support bars may extend laterally across the main body or extend longitudinally with the support bars in each modular unit being substantially aligned. In one preferred form, the main body may be carried on support legs so that the base thereof is raised above the ground or other support surface to define the space below the base. The side walls may, for example, be formed of a mesh material or be solid. The apparatus may further include a spray assembly disposed above or to the side of the main body for selective spraying of the waste material within the treatment chamber. There may further be provided covers or a roof structure which can overlie the main body.

According to another preferred form of the invention, the main body forms a unit and the apparatus includes a plurality of units disposed in spaced apart planes one above the other. Preferably, there is a plurality of units disposed in each plane.

In this multi-tier form of the invention, the apparatus may include a support frame which includes one or more support columns. In one arrangement, each unit may be mounted to the or each support column in cantilevered fashion. In another arrangement, each unit may be mounted to at least two support columns at opposite ends thereof. Preferably, there is further provided a track assembly operatively connected to the support frame and being adapted to receive a harvesting device thereon.

According to another embodiment the main body is in the form of a basket unit there being provided a plurality of units disposed one above the other. The apparatus further includes a mobile platform which is movable into a position whereby one of the basket units can be transferred onto the platform, the platform being movable to a position where the material within the basket can be harvested.

The apparatus of the present invention enables a continuous treatment and harvesting process to be effected. Waste material is fed to the treatment chamber through the open top. The upper section of the chamber forms a feed zone and the intermediate section of the chamber forms a treatment zone and the lower section forms a harvesting zone. The worms within the chamber progressively stabilise the material. The space beneath the base forms a harvest collecting zone, the material from the chamber being extracted through the base.

A second aspect of the present invention is related to a harvesting device which is suitable for use with the apparatus described above. Yet another aspect of the present invention relates to components suitable for use in the harvesting apparatus.

According to another aspect of the present invention there is provided a harvesting device which is suitable for use with the treatment apparatus described above. The harvesting device includes a carriage which is adapted to move within the space below the base of the main body and in a direction generally parallel with the support elements of the base, and a harvesting tool which includes a plurality of extraction elements which project outwardly, the arrangement being such that when in use the extraction elements are adapted to extend through the spaces between the support elements into the treatment chamber so as to dislodge and extract the material through the base.

In one preferred embodiment, the tool is mounted for rotation on the carriage about an axis of rotation which extends transversely.

In one preferred form, the tool includes an elongated rotor body mounted for rotation about its longitudinal axis. The rotor body may be generally circular in cross section and may be in the form of a cylinder or drum. Preferably, the extraction elements are arranged to extend generally radially of the outer surface of the rotor body. By radially is meant that the extraction elements project outwardly from the outer surface of the rotor body. The elements do not necessarily extend exactly radially in the mathematical sense and may for example, be inclined to the true radial axis.

In one form of the invention, the extraction elements comprise a series of blades each having a radially projecting arm section and a laterally extending blade section at the free end of each arm. The blade section may be dimensioned so that it is adapted to fit between the openings between adjacent support elements in the base of the apparatus.

In another form of the invention, the extraction element may comprise tines which extend generally radially of the outer surface of the rotor element of the tool.

In yet another form of the invention, the extraction elements may include a plurality of blades or tines at least some having associated therewith a radially extending brush element.

The harvesting tool need not necessarily be rotatable. For example, the tool may include a plurality of extraction elements in the form of blades mounted on a frame or carriage which is adapted to move beneath the base of the main body with the blades extending into the treatment chamber via the spaces between the support elements in the base.

In one preferred form of the invention the extraction elements are arranged in one or more groups with the elements in the or each group being spaced apart from one another and extending across the rotor body from one side to the other. In one preferred form, two groups of elements are provided with associated elements in each group being opposite to one another. The elements in each group may be arranged in a spiral configuration from one side of the rotor body to the other.

The harvesting device may further include a base upon which the carriage can move. The base may include a track section for the carriage and wheels for moving the base between a harvesting position and a delivery position in which material collected is transferred to a storage location. In another form the carriage may be operatively mounted to the main body such as for example, on a rail for movement and/or guidance relative thereto.

Drive means may be provided for moving the carriage along the base. Such drive means may include a drive motor for driving a rope or cable drum which is operatively connected to the base.

In another preferred form, the tool includes a plurality of extraction elements in the form of blades mounted on a frame or carriage which is adapted to move beneath the base of the main body with the blades extending into the treatment chamber via the spaces between the support elements in the base.

Preferably, the extraction elements are arranged in one or more groups with the elements in the or each group being spaced apart from one another and extending across the rotor body from one side to the other with two groups of elements are provided with associated elements in each group being opposite to one another, the elements in each group being arranged in a spiral configuration from one side of the rotor body to the other.

The device may further include a base upon which the carriage can move, the base including a track section for the carriage and wheels for moving the base between a harvesting position and a delivery position in which material collected is transferred to a storage location.

In yet another embodiment the carriage includes a frame which is adapted to be operatively connectable to a vehicle so that it can be raised or lowered and positioned within the space below the base of the main body of the apparatus, the tool including a plurality of blades at one end of the frame.

In yet another embodiment the device includes a main frame, wheels on the main frame which are adapted to run on tracks positioned relative to the main body of the apparatus so that the harvesting device can move beneath the base of the main body. The harvesting tool is operatively connected to the main frame, and a collecting receptacle is operatively connected to the main frame the receptacle having an open top side.

Preferably, the harvesting tool is disposed above the receptacle and movable relative thereto.

There are several types of harvesting devices described. It will be appreciated that the various forms of harvesting tool can be used on the various types of harvesting device. For example, the type of device which is operatively connectable to a vehicle can have a rotatable cutter thereon.

Preferably, the collecting receptacle includes a base which includes a conveyor means for discharging the harvested material from the receptacle. Preferably there is also provided a filling device for filling the treatment chamber, the filling device including a receptacle operatively connected to the main frame having an open top and a base, the base including conveying means for feeding material to a selected treatment chamber. It will be appreciated that the filling device may be completely separate from the harvesting device and operable totally independent thereof. This separate filling device may constitute a further distinct aspect of the invention.

Preferred embodiments of the invention will hereinafter be described with reference to the accompanying drawings, and in those drawings.

Referring to FIGS. 1 to 5 of the drawings, there is shown apparatus generally indicated at 10 which comprises a main body 12 in the form of a rectangular box shaped structure having mesh side walls 15 mounted to frame members 16. The main body 12 is supported on legs 17 so that it is spaced above the ground. There is further included supports 20 and a top bar 22 for supporting a spray pipe 19 (See FIG. 2).

Figure 1:
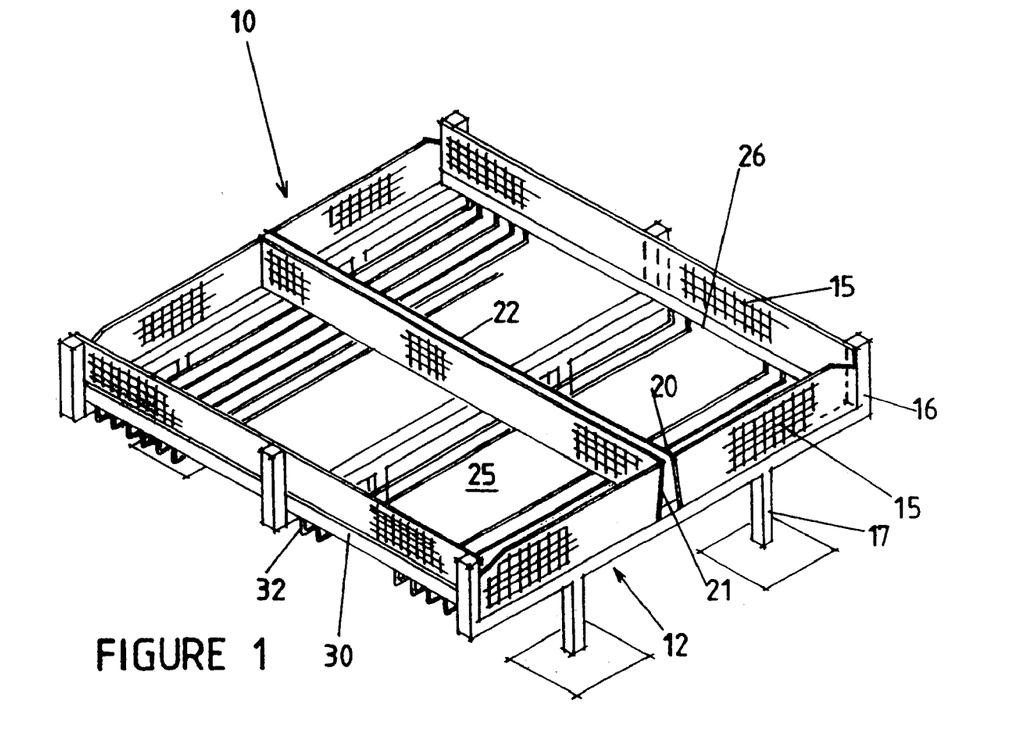
FIG. 1 is a schematic view of apparatus according to the present invention.

The main body 12 has a treatment chamber 25 therein with an open top 26 and a base 30. The treatment chamber is adapted to receive organic waste such as sewage sludge which is fed to the chamber via the open top and contains species of worms therein.

The base 30 includes a plurality of support elements 32 in the form of generally parallel U-shaped bars having arm portions 33 and a web portion 34. The arm portions 33 are welded to mounting plates 36 so as to form openings 35 therebetween. A cover or roof 18 may be provided over the top of the main body (see FIG. 2).

Figure 2:
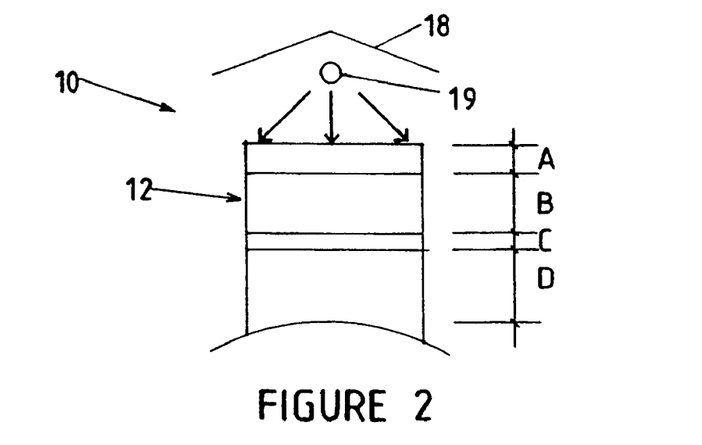
FIG. 2 is a diagram illustrating the various processes involved when the apparatus is in use.
Figures 3, 4, 5:
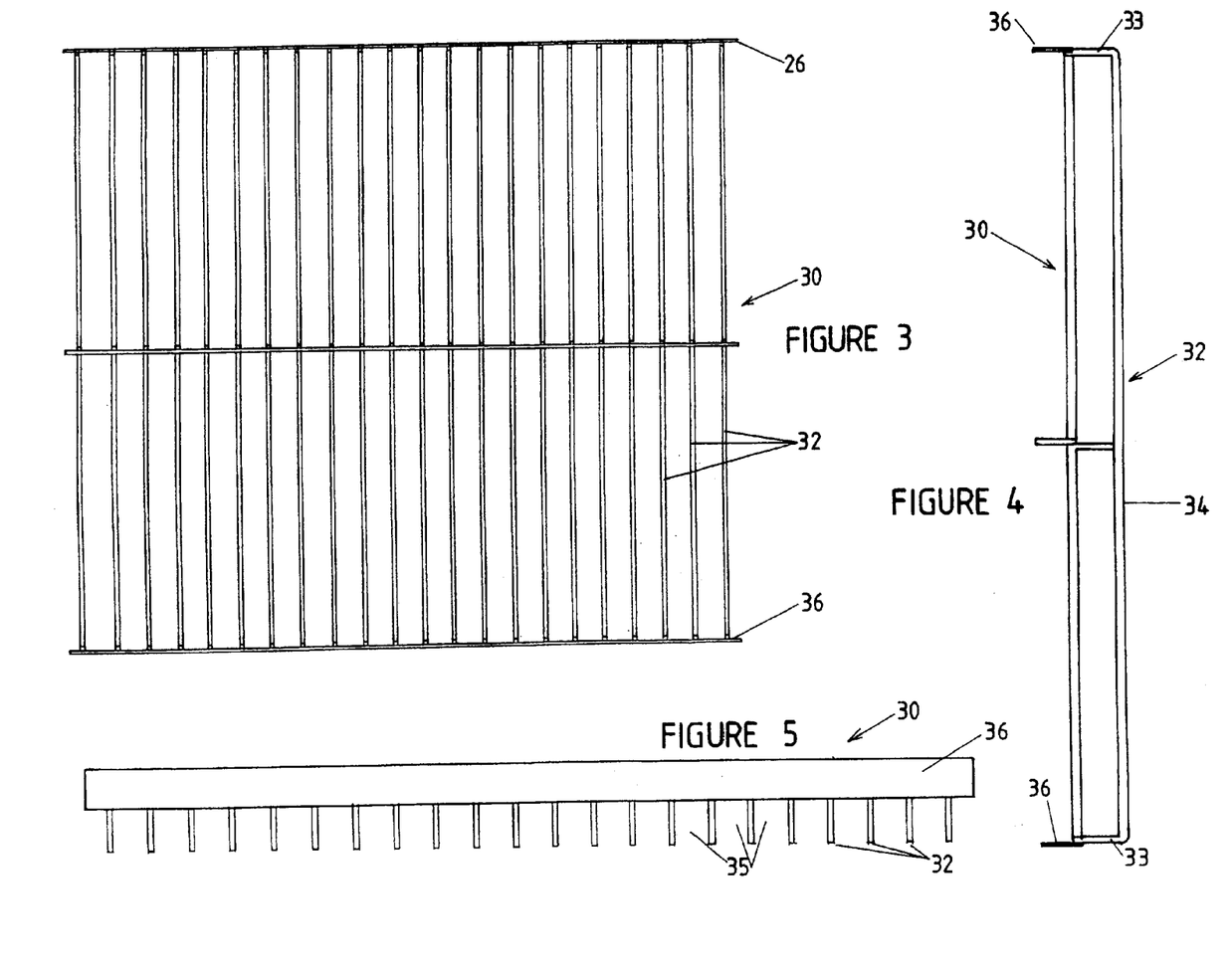
FIG. 3 is plan view of the base of the apparatus according to the present invention.
FIG. 4 is a side elevation of the base shown in FIG. 3.
FIG. 5 is an end elevation of the base shown in FIGS. 3 and 4.
Figure 6:
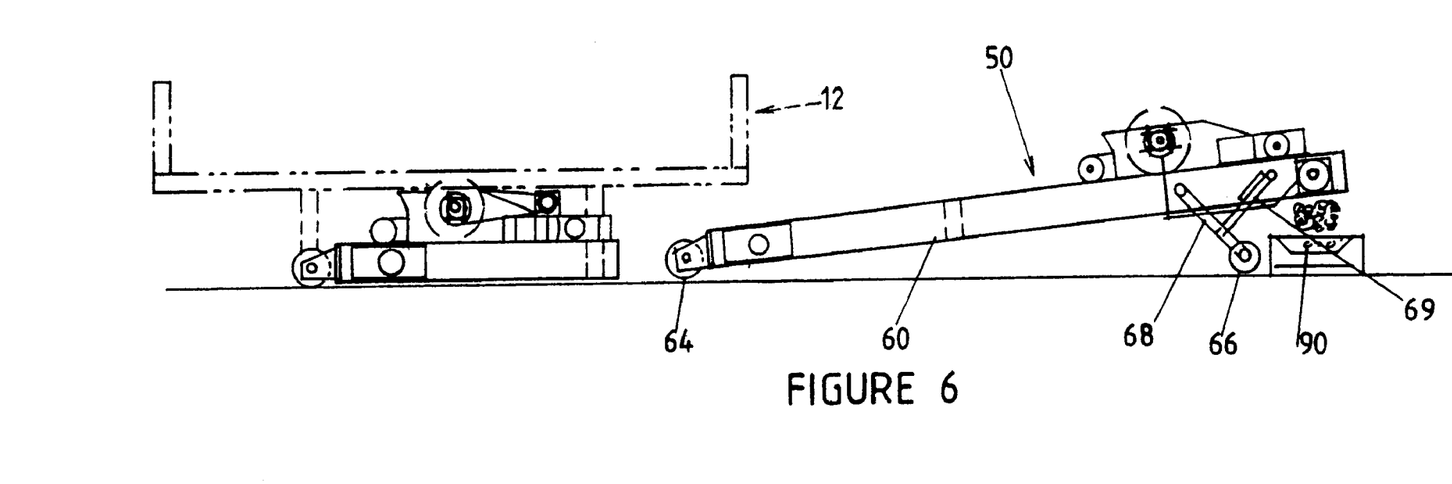
FIG. 6 is a schematic side elevation of harvesting apparatus according to the present invention.
Figure 7:
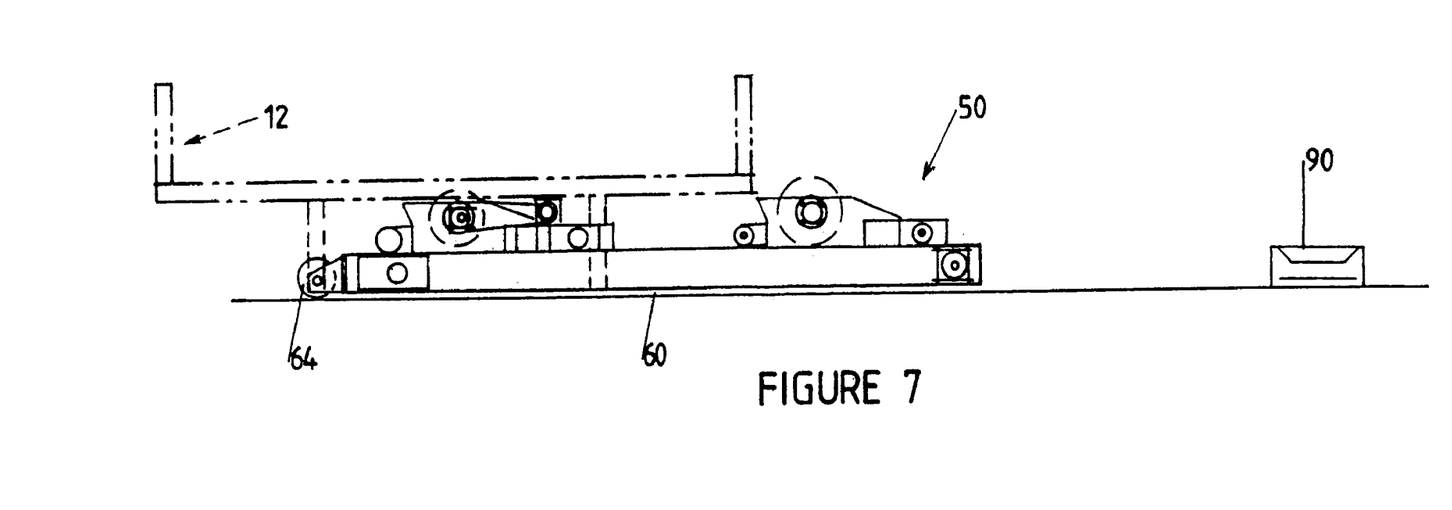
FIG. 7 is a similar view to that of FIG. 6 with the harvesting apparatus in a different position.
Figure 8:
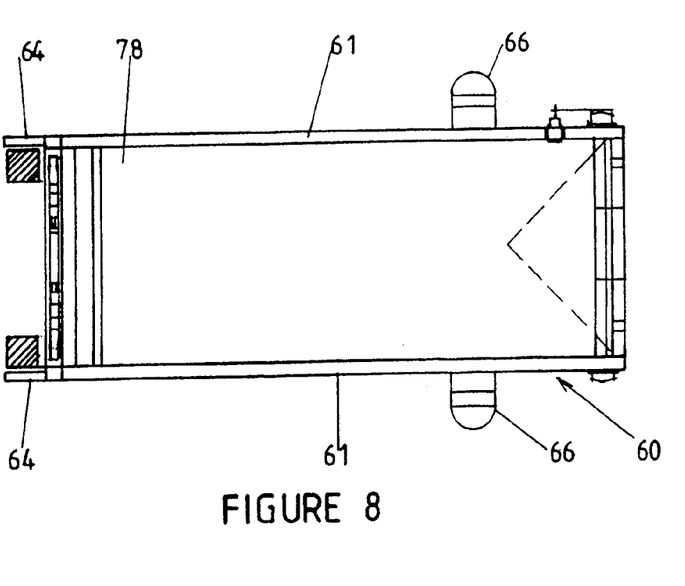
FIG. 8 is a plan view of part of the harvesting apparatus.
Figure 9:
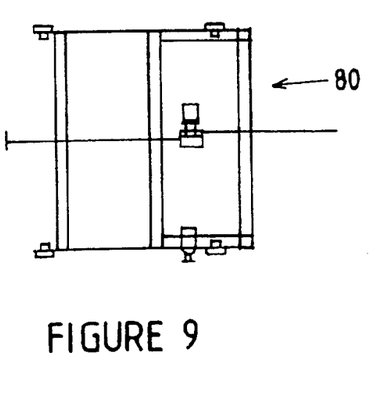
FIG. 9 is plan view of another part of the harvesting apparatus.
Figure 10:
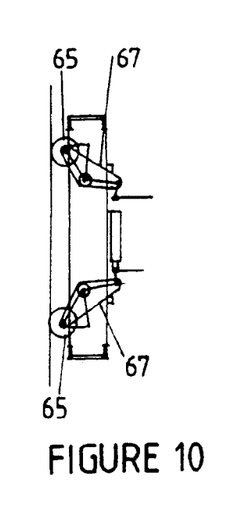
FIG. 10 is an end view of that part of the harvesting apparatus shown in FIG. 8.
Figure 11:
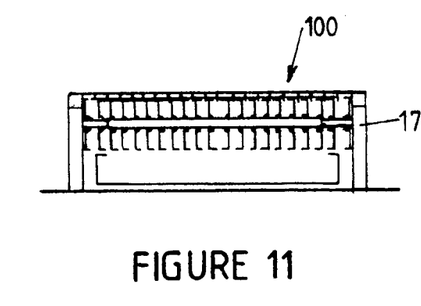
FIG. 11 is an end view of the two parts of the apparatus shown in FIGS. 8 and 9.
Figures 12, 14:
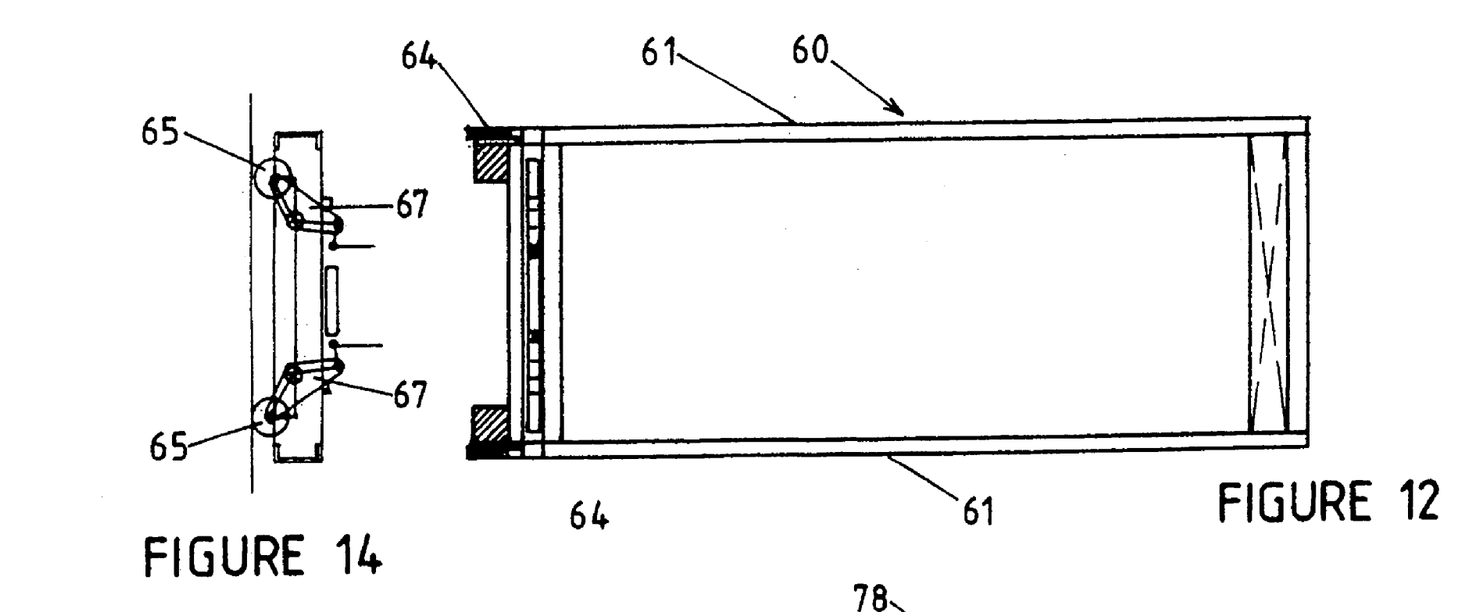
FIG. 12 is a plan view of harvesting apparatus according to another form of the present invention.
FIG. 14 is an end view of the apparatus shown in FIG. 12.
Figure 13:
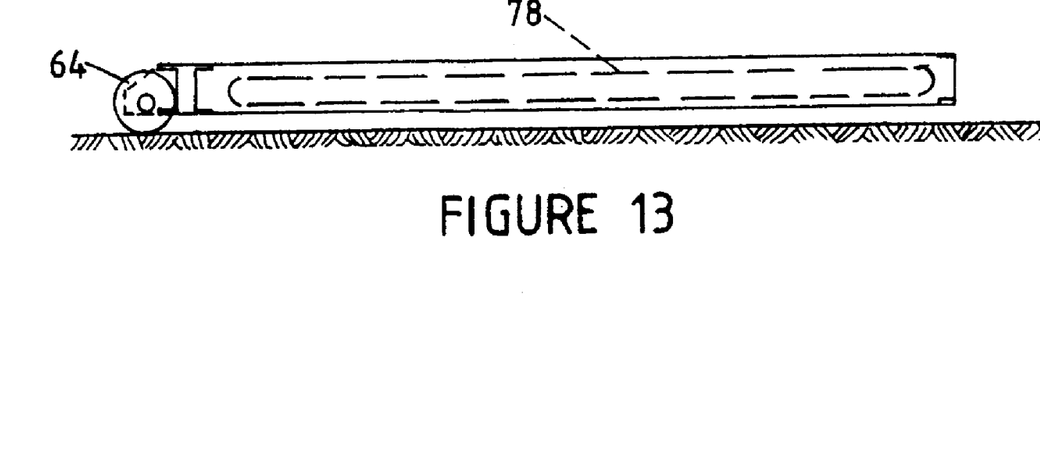
FIG. 13 is a side elevation of the harvesting apparatus shown in FIG. 12.
Figure 15:
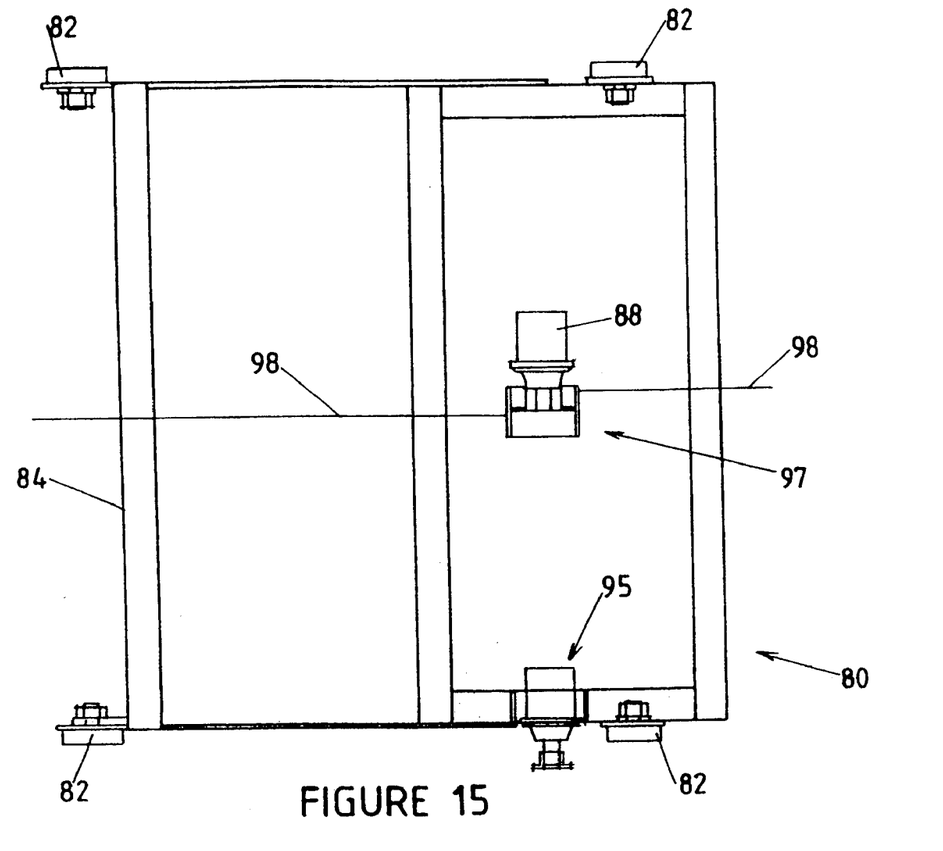
FIG. 15 is a plan view of a carriage according to one form of the present invention.
Figure 16:
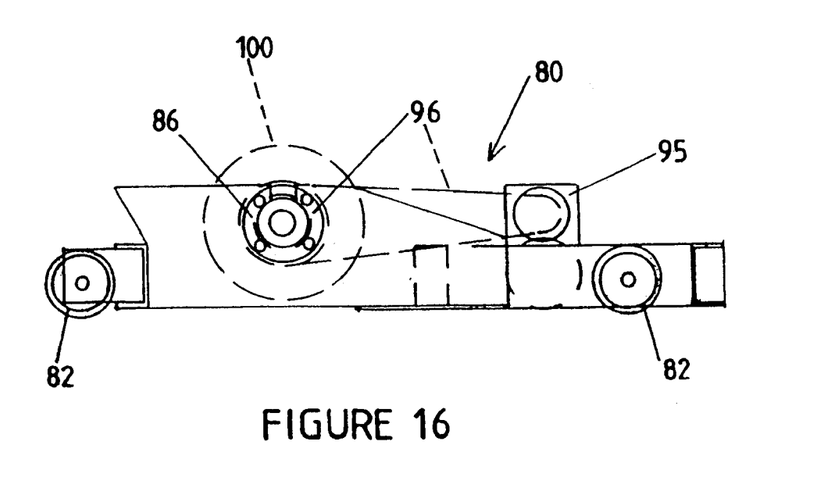
FIG. 16 is a side elevation of the carriage shown in FIG. 15.

The process is schematically illustrated in FIG. 2. Organic waste such as sewage sludge is fed to the treatment chamber 25 within main body 12 via the open top 26. The treatment chamber contains worms which progressively stabilize the waste material. The upper section A of the chamber defines a feeding zone and the intermediate section B defines a treatment zone and the lower section C defines a harvesting zone. When the waste material has been stabilized, it is harvested within the space below the base which defines an access or harvest collecting zone D, the material being extracted from the treatment chamber through the spaces between the support bars in the base.

Referring to, in particular, FIGS. 6 to 20 there is shown various embodiments of a harvesting device generally indicated at 50 which includes a base 60 having side rails which define a track 61, ground engaging wheels 64 and steering wheels 66, steering wheels being mounted on pivot arms 68 and arranged for actuation by piston cylinder 69. Alternatively, the wheels may be mounted on a telescopic leg.

The base 60 is movable between a harvesting position in which it is disposed beneath the main body 12 of the treatment apparatus and a delivery position in which harvested material which is collected on the base 60 can be transferred for example, to a transport conveyor 90. In the delivery position the steering wheels are raised by pivot arms 68 so that the end of the base 60 is disposed above the transport conveyor 90.

The base 60 includes a conveyor 78 which collects the harvested material thereon and transfers it to the transport conveyor 90. The base 60 further includes lateral locating wheels 65 which are mounted to pivot arms 67 which where actuated cause the wheels 65 to lift the base 60 and permit lateral movement thereof.

A carriage 80 is disposed on the base and includes track engaging wheels 82, a main body or frame 84, a tool mounting section 86 and drive motor for driving the carriage and a drive motor for driving a tool 100.

The carriage 80 is adapted to run along rails 61 of the base 60. The carriage 80 includes a drive motor 88 mounted so as to drive rope drum 97. The rope or cable 98 on the rope drum is operatively connected to the ends of the base 60 so that rotation of the drum will cause movement of the carriage 80 along the rails in a forward or rearward direction As best shown in FIGS. 17 to 20 and 32, the tool 100 is mounted for rotation on the carriage and drive by drive motor 95 through transmission 96 in the form of a chain and sprocket mechanism.

Figure 17:
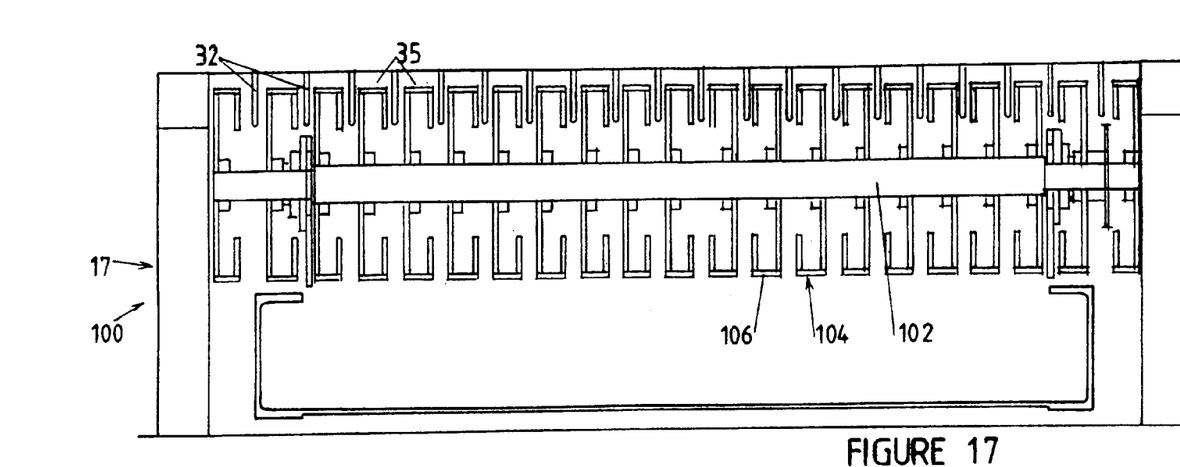
FIG. 17 is a side elevation of harvesting tool according to one form of the present invention.
Figure 18:
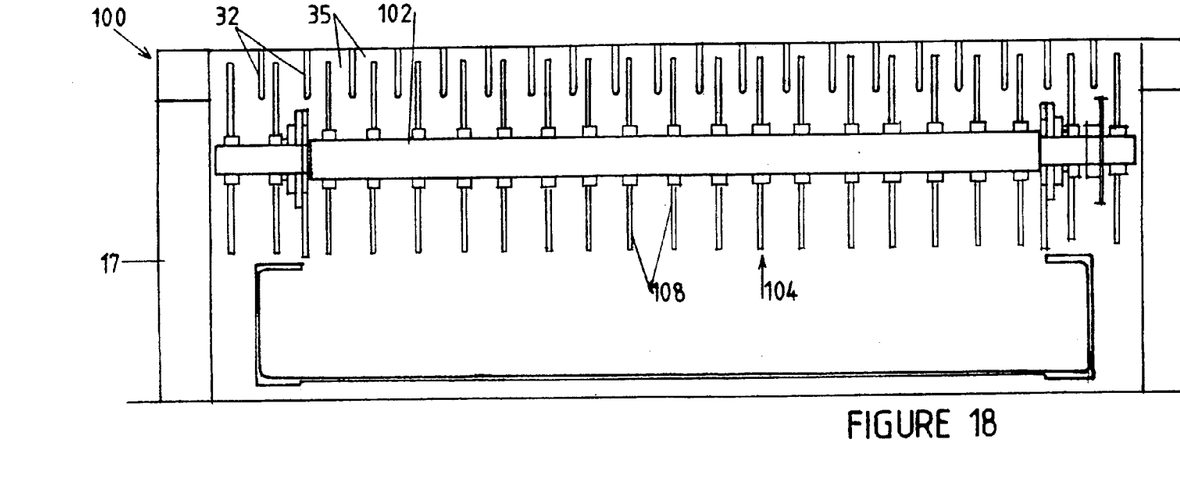
FIG. 18 is a side elevation of a harvesting tool according to another form of the present invention.
Figures 19, 20:
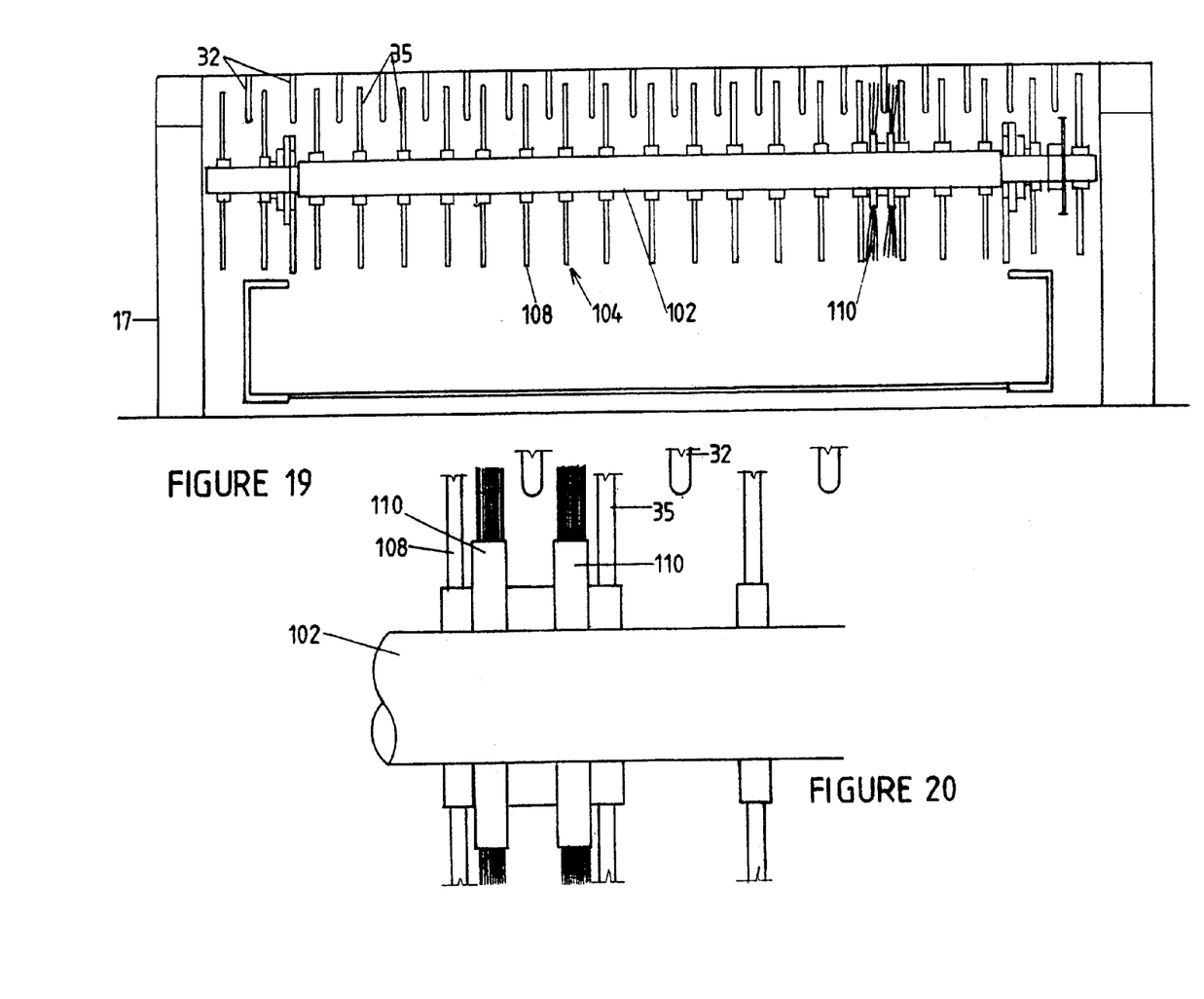
FIG. 19 is a side elevation of a harvesting tool according to yet another form of the present invention.
FIG. 20 is a detail of part of the tool shown in FIG. 19.
Figure 32:
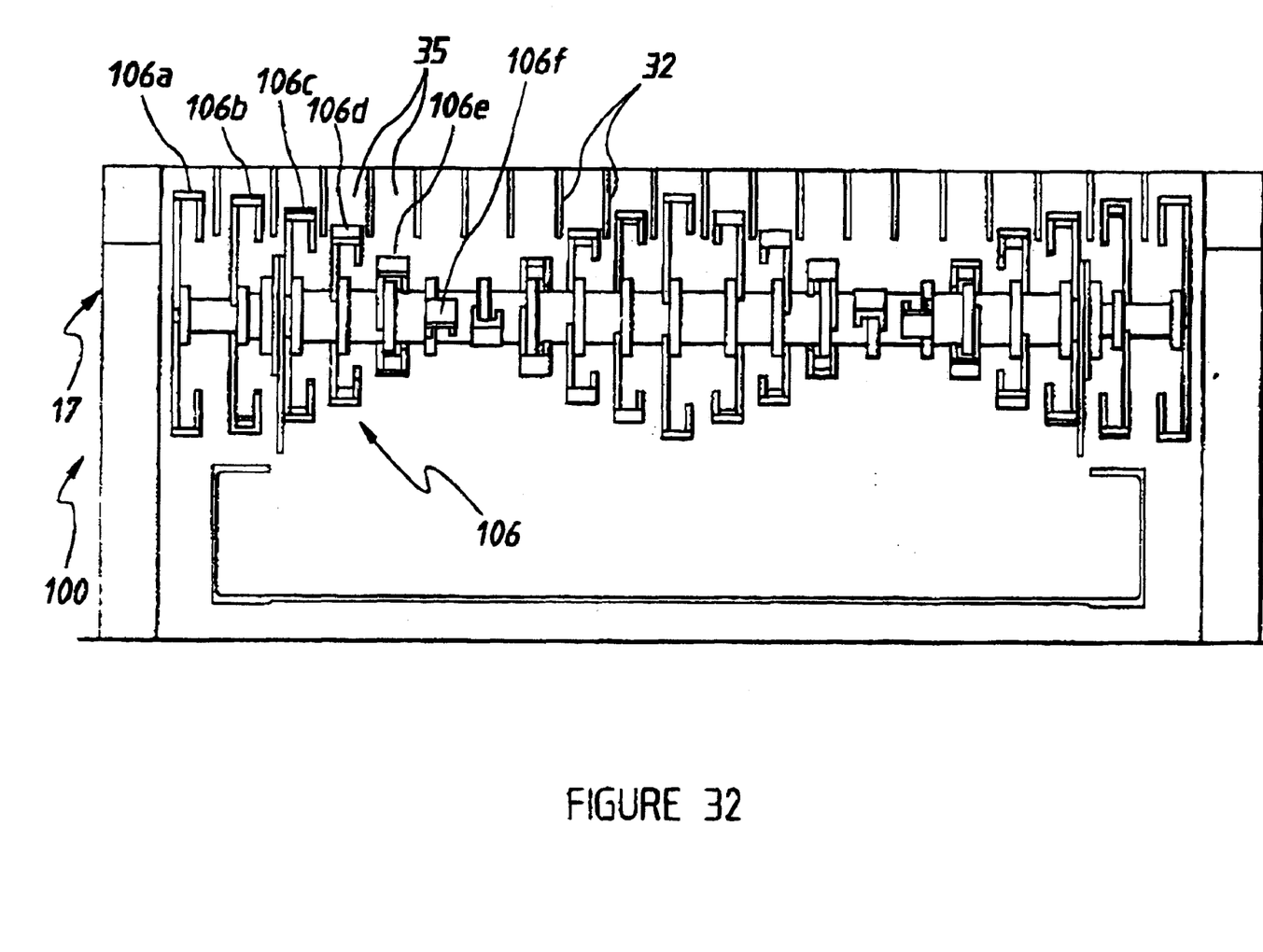
FIG. 32 is a similar view to FIG. 17 showing the blades in a spiral configuration.

The tool generally indicated at a 100 includes a rotor section 102 having a plurality of extraction elements 104 thereon. In the embodiment of FIG. 17, the extractions elements are in the form of blades 106. In the embodiment of FIG. 18, the extractions elements are in the form of tines 108 and in the embodiment of FIGS. 19 and 20, the extraction elements include tines 108 and brushes 110. As shown in FIG. 32 adjacent blades 106 are circumferentially offset with respect to one another. That is, when viewed from one end blade 106a is upright, blade 106b is offset from the upright blade 106a. Blades 106c, 106d and 106e are circumferentially offset to one another and blade 106f is at right angles to blade 106a. As can be seen therefore the blades form a spiral around the rotor section 102.

In the harvesting operation, the base 60 is disposed in the space beneath the main body 12 with its rails 61 being generally parallel with material support elements 32 and with the extraction elements 104 of the tool 100 aligned with the openings 35 at the ends of the material support elements. Once the base 60 and carriage 80 are correctly positioned relative to the base of the main body 12 the carriage 80 is moved along the rails 61 with the tool 100 rotating. As the carriage 80 moves into the space beneath the main body 12 the extraction elements 104 pass through the openings 35 and into the treatment chamber in the spaces between the support elements 32. The extraction elements cause dislodgement of the treated material which falls through the base 30 of the main body 12 onto conveyor 78 on the base 60 of the harvesting device. The base 60 can then be withdrawn and positioned for transfer of the harvested material from conveyor 78 to transport conveyor 90.

Figure 21:
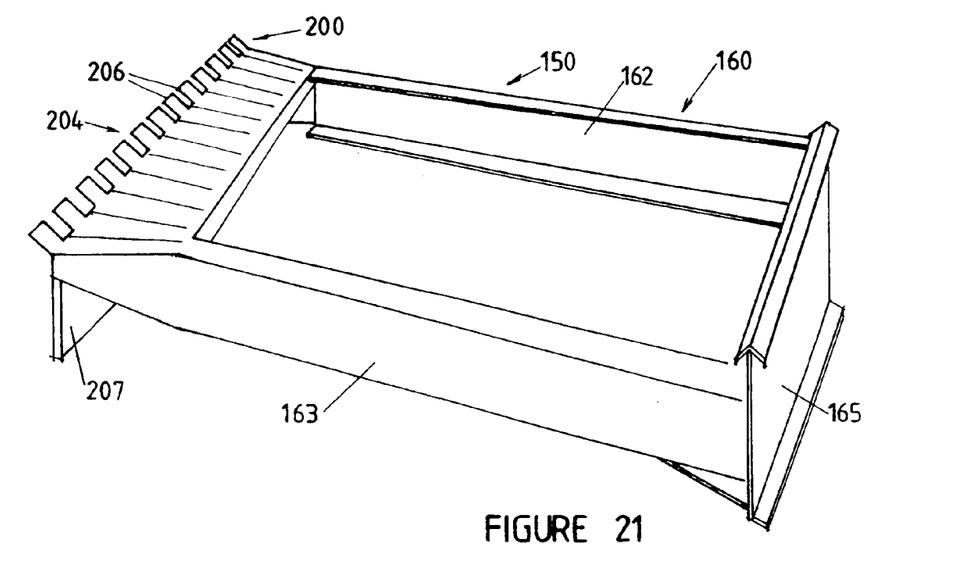
FIG. 21 is a schematic perspective view of harvesting apparatus according to yet another embodiment of the present invention.
Figure 22:
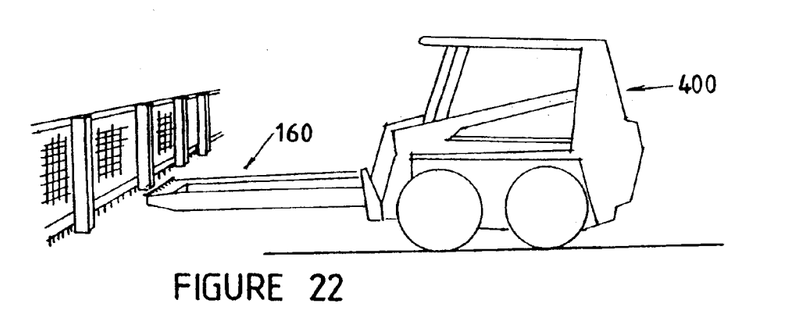
FIGS. 22 and 23 are schematic views of the harvesting apparatus shown in FIG. 21 when in use.
Figure 23:
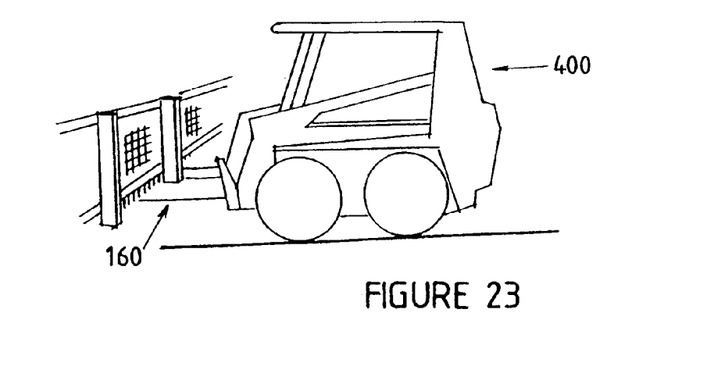

A further embodiment of harvesting device according to the present invention is shown in FIGS. 21 to 23. The harvesting device generally indicated at 150 includes a main frame 160 comprising side members 162 and 163 and a mounting section 165. The mounting section is adapted to be secured to a vehicle 400 so that it can be moved forwards or backwards or be raised or lowered.

The device further includes a harvesting tool 200 at the forward end of the frame 160. The tool 200 includes a series of upwardly projecting extraction elements 204 in the form of blades 206. A scraper blade 207 projects downwardly from the frame 160.

In the harvesting operation the main frame 160 of the device is mounted to the vehicle and then positioned in the space beneath the main body 12 for movement generally parallel with material support elements 32 and with the extraction elements 204 of the tool 200 aligned with the openings 35 at the ends of the material support elements. Once the frame 160 is correctly positioned relative to the base of the main body 12, the frame is raised so that the elements 204 pass through the openings 35 and into the treatment chamber in the spaces between the support elements 32. The vehicle is then reversed and the extraction elements cause dislodgement of the treated material. Extraction may also be effected by forward movement of the vehicle. Furthermore, the elements 204 may be replaced by a rotatable extraction tool.

Figure 24:
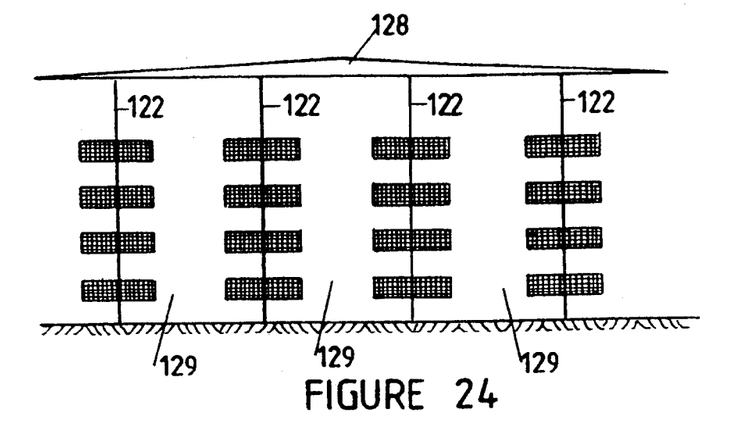
FIG. 24 is a schematic side elevation of apparatus according to yet another embodiment of the present invention.
Figure 25:
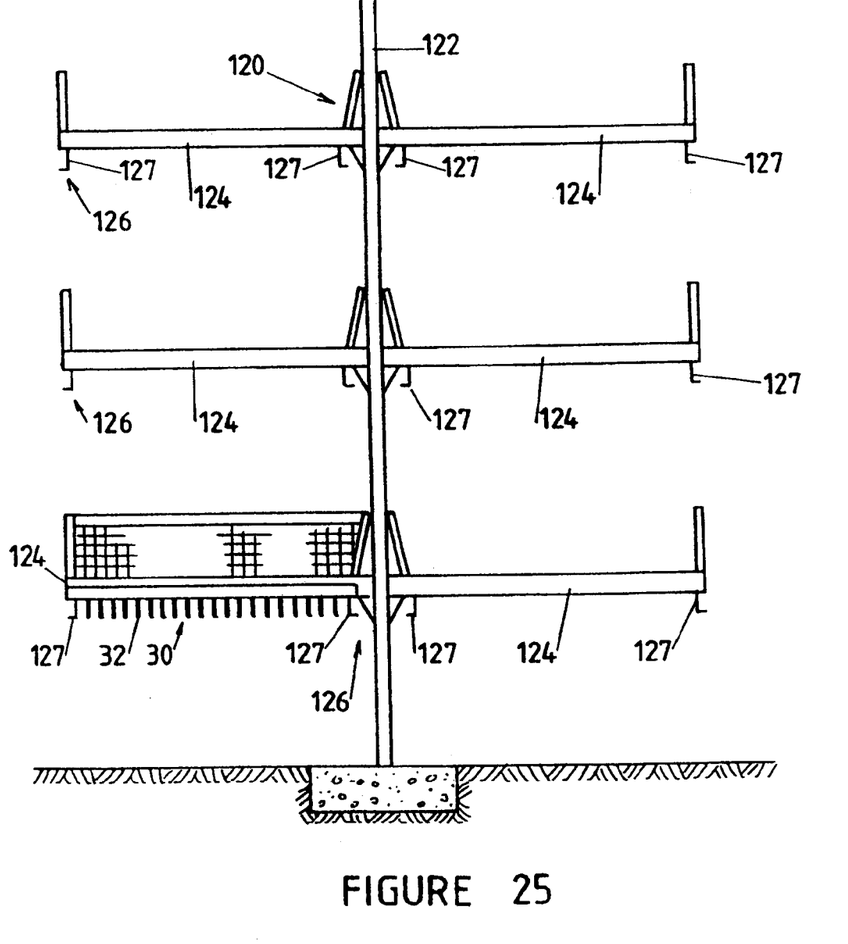
FIG. 25 is a schematic detail of the apparatus shown in FIG. 24.

Referring to FIGS. 24 and 25, there is shown a multi-tiered system wherein the units are supported in different planes and in rows by a support frame 120 which includes a plurality of upright columns 122 and a series of platforms 124 arranged in cantilevered fashion on the columns. The platforms 124 may form part of the units or simply provide a support for the units. The support elements 32 of the base 30 project downwardly from the platforms 124. The platforms 124 are arranged in groups one above the other and there is a space between the units in each plane. A roof 128 covers the support frame 120. A series of laneways 129 are provided between the groups of units.

The system further includes a track assembly 126 associated with each platform 124 and includes a pair of tracks 127 in the form of channels for carrying a harvesting tool which may for example be of the type described with reference to FIG. 31.

Figure 26:
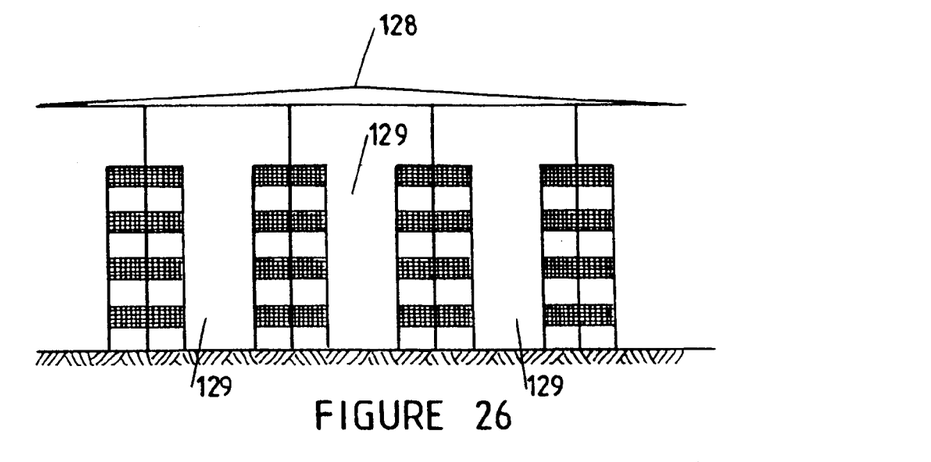
FIG. 26 is a schematic side elevation of apparatus according to yet another embodiment of the present invention.
Figure 27:
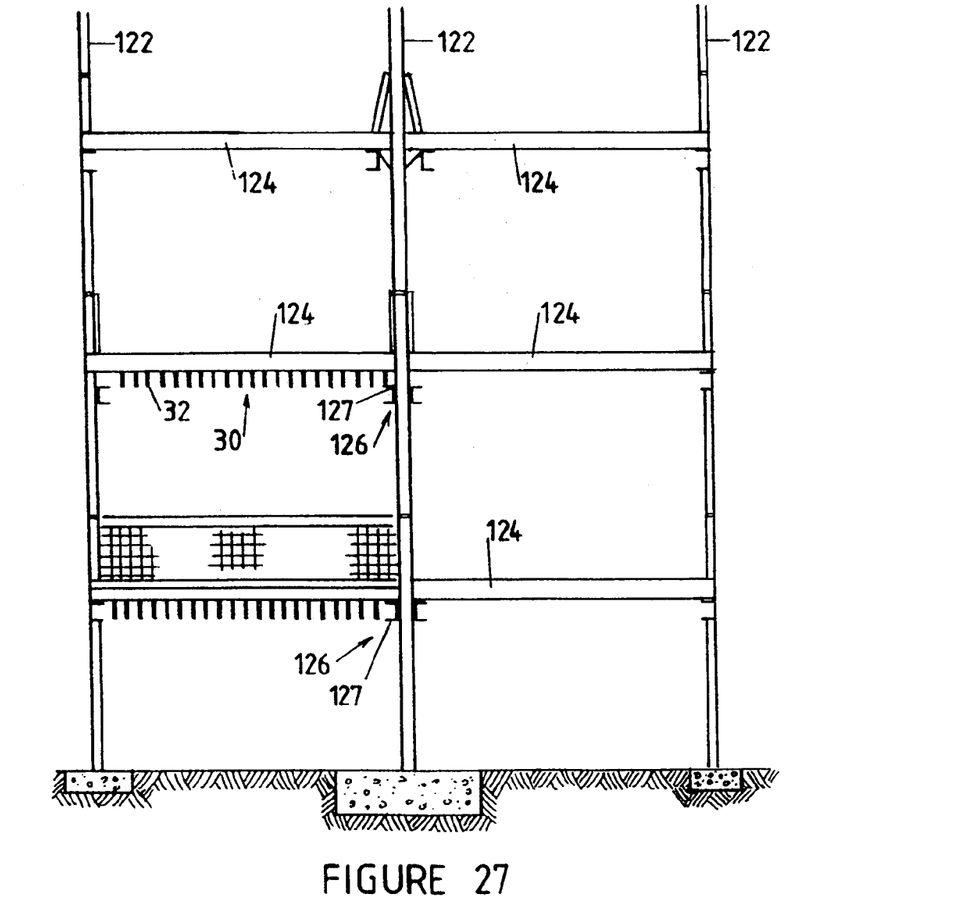
FIG. 27 is a schematic detail of the apparatus shown in FIG. 26.

The system shown in FIGS. 26 and 27 is essentially the same as that described in FIGS. 24 and 25 and like reference numerals have been used to describe like parts. In this particular system however, each platform is supported between upright columns 122.

Figure 28:
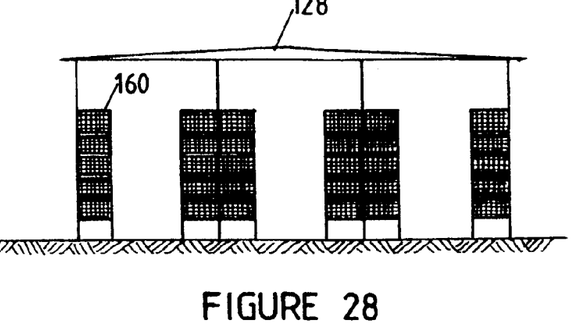
FIG. 28 is a schematic end elevation of apparatus according to yet another embodiment of the present invention.
Figure 29:
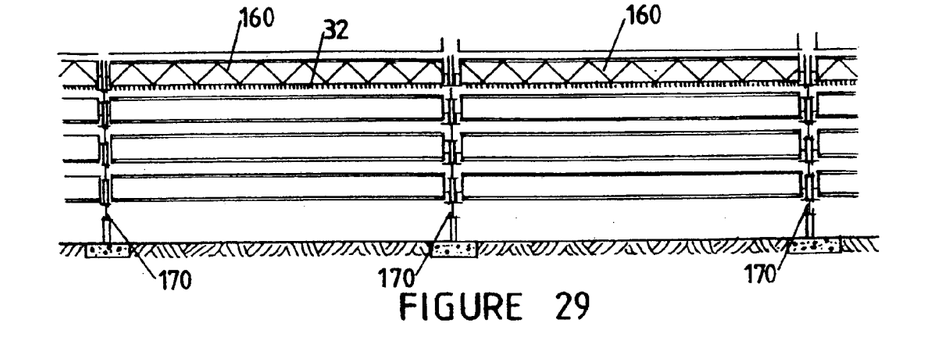
FIG. 29 is a partial schematic side elevation of the apparatus shown in FIG. 28.
Figure 30:
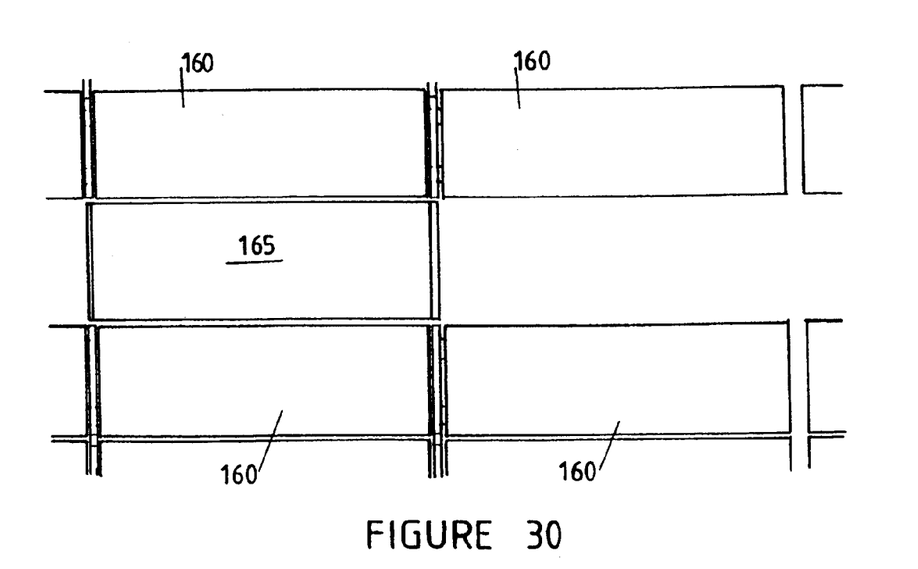
FIG. 30 is a plan view of the apparatus shown in FIGS. 28 and 29.

Referring to FIGS. 28 to 30 this also shows a multi-tiered system. This system relies on the units being large individual baskets 160. Each unit is relatively large and may be, for example, 6 m long, 1.8 m wide and 700 mm deep. (The support elements 32 on the base 30 to run across the 1.8 m width of the bed.) The sides of the basket are constructed to form a beam or truss able to span the 6 m when fully loaded as described earlier. At the basket ends there are wheels similar to rail bogies which allow the basket to be pulled out from the support frame for feeding, monitoring, etc. The support frames include a tower/column structure that has rails at levels to allow the roll on and roll off these large baskets. These will be rolled onto and off a large platform 165 able to be raised and moved into position for each basket so that the basket on the platform can be transferred to a harvesting location.

The baskets can be stacked, for example, 5 high with 11 baskets in a row with the whole system having 4 rows of towers, two towers with two baskets across per level and the two outer towers having a single width of baskets. At the top of each of the towers a connecting member can be included to provide additional stability and can be used to provide support for the roof structure.

Figure 31:
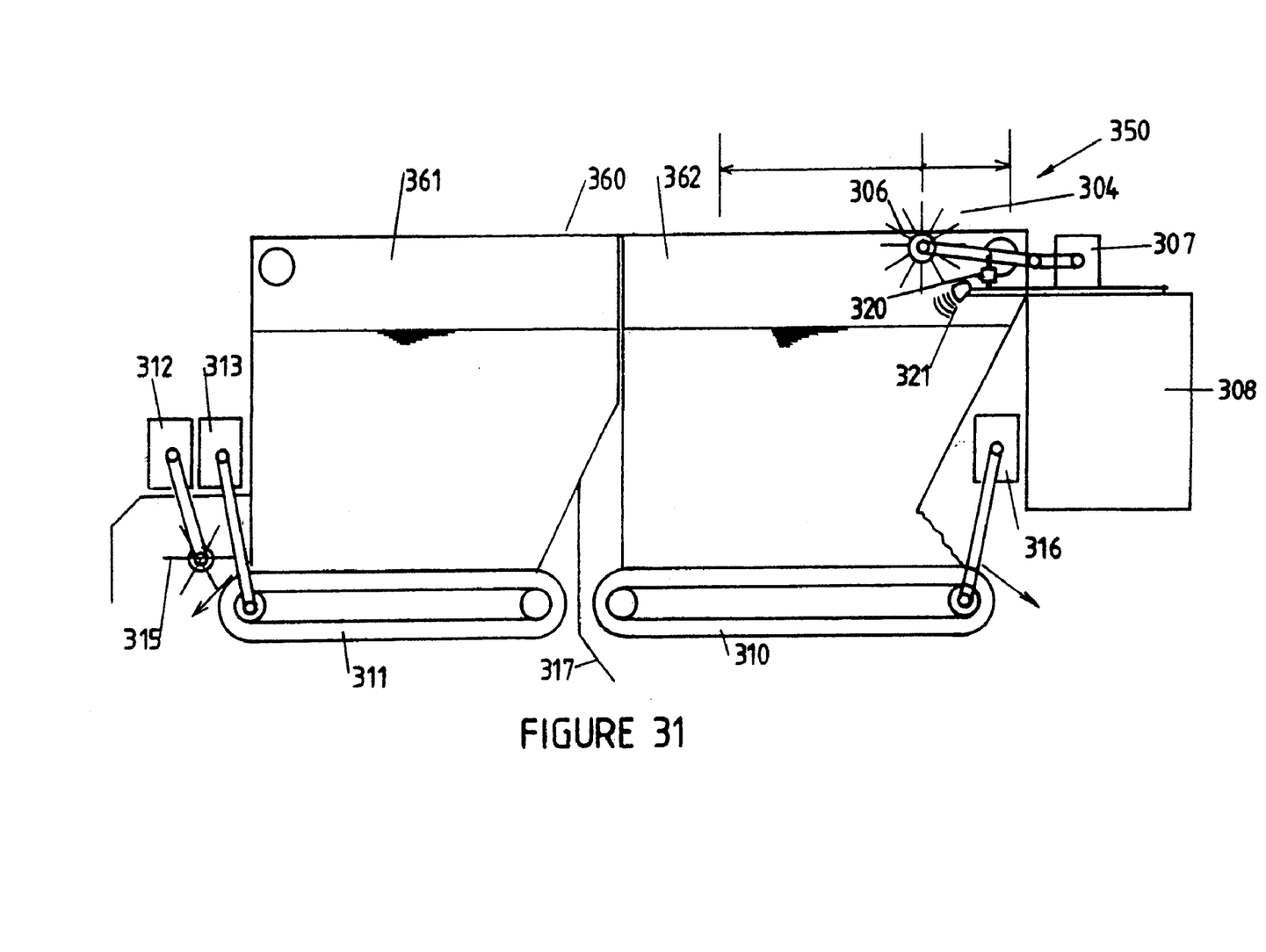
FIG. 31 is a schematic side elevation of yet another embodiment of harvesting apparatus according to the present invention.

FIG. 31 illustrates a harvesting device which is suitable for use with the multi-tier systems described with reference to FIGS. 25 to 29. The harvesting device generally indicated at 350 includes a main frame 360 having wheels 303 thereon which are adapted to run on tracks 127 as shown in FIGS. 24 to 27. There are further provided two open topped receptacles 361 and 362 which are secured to and depend below the main frame 360. One of these receptacles 362 is used for collecting the harvested material and the other 361 is used for a filling operation.

Each receptacle has a conveyor 310 and 311 in the base thereof for discharging material from the respective receptacle. The conveyors 310 and 311 are driven by respective drive mechanisms 313 and 316.

The receptacle 361 which is used in the filling operation has associated therewith a rotatable flinging device 315 driven by drive mechanism 312. The device 313 is shown rotatable about a horizontal axis. It may also in another form be rotatable about a vertical axis. A rake 317 is provided for raking the material.

The device further includes a harvesting tool 306 which includes a rotatable member having tines thereon. The tool 306 is driven by drive 307 which causes rotation of the tool as well as movement relative to the receptacle 362 shown by the arrow. A height adjustment device 320 raised or lowers the tool 306 and a sensor 321 senses the level of the material within the receptacle. All systems are powered by power unit 308.

The tools used in each device shown may be interchangeable.

Finally, it is to be understood that various alterations, modifications and/or additions may be incorporated into the various constructions and arrangements of parts without departing from the spirit or ambit of the invention.

What is claimed is:

1. A harvesting device which is suitable for use with waste treatment apparatus of the type including an elevated main body supporting a base composed of a plurality of spaced-apart parallel support elements defining the bottom of a treatment chamber within the main body, said harvesting device comprising a carriage which is adapted to move within the space below the base of the main body in a direction generally parallel with the support elements of the base, and a harvesting tool supported by the carriage and which includes a plurality of extraction elements which project outwardly, the arrangement being such that when in use, the extraction elements are adapted to extend through the spaces between the support elements into the treatment chamber so as to dislodge and extract the material from the treatment chamber through the base, said extraction elements being arranged in one or more groups with the elements in the or each group being spaced apart from one another and extending across the tool from one side to the other with two groups of elements being provided, with associated elements in each group being opposite to one another, the elements in each group being arranged in a spiral configuration from one side of the tool to the other.

2. A harvesting device according to claim 1 wherein the tool is mounted for rotation on the carriage about an axis of rotation which extends transversely.

3. A harvesting device according to claim 2 wherein the tool includes an elongated rotor body mounted for rotation about its longitudinal axis.

4. A harvesting device according to claim 3 wherein the rotor body is generally circular in cross section and in the form of a cylinder or drum.

5. A harvesting device according to claim 4 wherein the extraction elements are arranged to extend generally radially of the outer surface of the rotor body.

6. A harvesting device according to claim 5 wherein the extraction elements include a series of blades each having a radially projecting arm section and a laterally extending blade section at the free end of each arm, the blade section being dimensioned so that it is adapted to fit between the openings between adjacent support elements in the base of the treatment apparatus.

7. A harvesting device according to claim 6 wherein the extraction elements include tines which extend generally radially of the outer surface of the rotor body of the tool.

8. A harvesting device according to claim 6 wherein the extraction elements include a plurality of blades or tines at least some having associated therewith a radially extending brush element.

9. A harvesting device according to claim 5 further including a base upon which the carriage can move, the base including a track section for the carriage and wheels for moving the base between a harvesting position and a delivery position in which material extracted by the extraction elements is transferred to a storage location.

10. A harvesting device according to claim 1 wherein the tool includes a plurality of extraction elements in the form of blades mounted on said carriage which is adapted to move beneath the base of the main body with the blades extending into the treatment chamber via the spaces between the support elements in the base.

11. A harvesting device which is suitable for use with waste treatment apparatus of the type including an elevated main body supporting a base composed of a plurality of spaced-apart parallel support elements defining the bottom of a treatment chamber within the main body, said harvesting device including a carriage which is adapted to move within the space below the base of the main body in a direction generally parallel with the support elements of the base, and a harvesting tool supported by the carriage and which includes a plurality of extraction elements which project outwardly, the arrangement being such that when in use the extraction elements are adapted to extend through the spaces between the support elements into the treatment chamber so as to dislodge and extract the material from the treatment chamber through the base, wherein the carriage includes a frame which is adapted to be operatively connected to a vehicle so that it can be raised or lowered and positioned within the space below the base of the main body of the treatment apparatus, the tool including a plurality of blades at one end of the frame.

12. A harvesting device according to claim 11 including a main frame, wheels on the main frame which are adapted to run on tracks positioned relative to the main body of the treatment apparatus so that the harvesting device can move beneath the base of the main body, the harvesting tool being operatively connected to the main frame, and a collecting receptacle operatively connected to the main frame and having an open top side.

13. A harvesting device according to claim 12 wherein the harvesting tool is disposed above the receptacle and is movable relative thereto.

14. A harvesting device according to claim 13 wherein the collecting receptacle includes a base which includes a conveyor means for discharging the harvested material from the receptacle.

15. A harvesting device according to claim 14 including a filling device for filling the treatment chamber, the filling device including a receptacle operatively connected to the main frame and having an open top and a base, the base including conveying means for feeding materials to a selected treatment chamber.

* * * * *